United States Patent [19]

Hagedorn

[11] 4,272,477

[45] Jun. 9, 1981

[54] APPARATUS FOR PREPARATION OF SOLUTIONS OF SOLID SAMPLES FOR WET CHEMICAL ANALYSIS

[75] Inventor: Fritz Hagedorn, Sehnde, Fed. Rep. of Germany

[73] Assignee: Kali-Chemie Aktiengesellschaft, Hanover, Fed. Rep. of Germany

[21] Appl. No.: 48,188

[22] Filed: Jun. 13, 1979

[30] Foreign Application Priority Data

Jul. 6, 1978 [DE] Fed. Rep. of Germany ....... 2829690

[51] Int. Cl.³ ........................... G01N 1/04; G01N 1/28
[52] U.S. Cl. ........................................ 422/50; 73/863; 422/62; 422/261; 422/268
[58] Field of Search ................... 422/50, 68, 261, 268, 422/65, 62; 73/421 R; 23/230 A

[56] References Cited

U.S. PATENT DOCUMENTS

| | | | |
|---|---|---|---|
| 2,701,210 | 2/1955 | Fisher et al. | 23/230 A |
| 2,953,440 | 9/1960 | Claudy | 422/62 |
| 2,979,385 | 4/1961 | Karasek | 422/62 |
| 3,545,281 | 12/1970 | Johnston | 73/432 |
| 3,620,675 | 11/1971 | Olson | 422/68 |

FOREIGN PATENT DOCUMENTS

| | | |
|---|---|---|
| 1103039 | 3/1961 | Fed. Rep. of Germany . |
| 2242056 | 10/1973 | Fed. Rep. of Germany . |
| 2257824 | 6/1974 | Fed. Rep. of Germany . |
| 1648128 | 10/1974 | Fed. Rep. of Germany . |
| 2558377 | 7/1976 | Fed. Rep. of Germany . |
| 2559014 | 7/1977 | Fed. Rep. of Germany . |

OTHER PUBLICATIONS

Imperial Chemical Industries, Publication EDN 2238, Mar. 1976.

*Primary Examiner*—Ronald Serwin
*Attorney, Agent, or Firm*—Schwartz, Jeffery, Schwaab, Mack, Blumenthal & Koch

[57] ABSTRACT

Apparatus for preparing solutions of solid samples for wet chemical analysis comprising an overflow dissolving vessel divided by an overflow baffle into at least two chambers, means for maintaining a constant stream of solvent flowing successivefully through the chambers of said overflow dissolving vessel and a metering conveyor scale for continuously metering a measured amount of solid sample to be analyzed to the overflow dissolving vessel, said metering conveyor scale comprising a conveyor for continuously introducing solid sample into the dissolving vessel, a vibratory feeder for continuously supplying solid sample to the conveyor at a controlled rate and an overflow funnel for supplying a controlled amount of sample to the vibratory feeder; deflecting baffles and agitators are provided to promote mixing and dissolution of the sample and means are provided for automatically withdrawing a sample of solution for analysis from the chamber remote from the chamber into which the solid sample is introduced.

10 Claims, 3 Drawing Figures

APPARATUS FOR PREPARATION OF SOLUTIONS OF SOLID SAMPLES FOR WET CHEMICAL ANALYSIS

This invention relates to an apparatus for preparation of solid samples for wet chemical analysis, comprising a dissolving vessel with an associated solvent supply and a metering device for measuring a sample, taken from a larger batch to be analyzed, into the dissolving vessel.

BACKGROUND OF THE INVENTION

In process monitoring and control and in the inspection and quality control of end products in numerous industrial plants, on-line analysis is becoming increasingly important. Within the narrow field of analytical indication, the problems encountered may be overcome for the most part by means of available analytical methods, such as for example titrimetric, photometric, conductometric, or thermometric analysis. Also, the degree of automation of such analytical methods is very highly developed. The basic requirement for all of these analytical methods is the availability of a solution of the sample. This regularly results in difficulties whenever solid samples are to be analyzed. To be sure, it is possible by means specially adapted to particular problems, but otherwise commercially available, to obtain a sample of a larger batch which is thoroughly representative of the composition of the batch. Such samples, however, are only roughly defined in amount. Except in manual methods which are time and labor intensive and consequently expensive, the problem of accurately weighing all or part of a sample, discarding possible residues and quantitatively transferring the weighed sample into a suitable dissolving vessel, has remained largely unsolved.

There has been no lack of attempts in the past to solve this problem by mechanized or automated means. The starting point of the invention is a device of the type used specifically for the analysis of NPK fertilizers, which exist in the form of homogeneous dust-free granules. In this program controlled device, the sample which is furnished by the sampler in a discontinuous manner and only roughly defined with respect to its amount, is transferred to a funnel from whence a vibrator conveyor feeds the maaterial into a scale pan rotatable by 180° around a horizontal axis, of a photomechanically controlled inclination balance. As soon as a predetermined amount of the sample has been accumulated in the scale pan, the vibrator conveyor is swung away, the scale pan is rotated by 180° and the sample is tipped into a dissolving vessel in which a predetermined amount of solvent has previously been deposited from a solvent tank by means of an automatic pipette. The sample is dissolved therein; part of the solution is drawn off for the actual analysis; the remainder is discarded, and the dissolving vessel is rinsed, after which a new cycle may be started. In addition to the fact that this device is suitable only for samples which are absolutely dust free, have no tendency to stick and are largely homogeneous with respect to grain size, its design, its controls and its control programs are complicated, and it is therefore prone to malfunctions and/or disturbances.

OBJECTS OF THE INVENTION

Accordingly, it is an object of the present invention to provide an improved sample measuring device which may be used with materials which tend to dust.

It is also an object of the present invention to provide an improved sample measuring device which may be used with materials which tend to bake onto their supporting surfaces.

Another object of the present invention is to provide an improved sample measuring device which may be used with samples exhibiting a broad spectrum of grain sizes.

It is still another object of the present invention to provide an improved sample measuring device which avoids or eliminates a large number of program steps.

A further object of the present invention is to provide an improved sample measuring device which is less prone to disturbance and/or malfunction.

SUMMARY OF THE INVENTION

These and other objects of the invention are achieved by providing an apparatus for preparing solutions of solid samples for wet chemical analysis comprising a dissolving vessel, means for maintaining a constant stream of solvent flowing through said dissolving vessel, and means for a continuously metering a measured amount of a sample to be analyzed to the dissolving vessel.

According to a preferred form of the invention, there is provided metering device comprising a metering conveyor scale which continuously supplies a measured sample to a dissolving vessel which consists of an overflow vessel through which a constant flow of solvent is passed.

The metering conveyor scale continuously meters the sample, discontinuously supplied by the sampler, in a constant flow into the overflow vessel, with a constant flow of solvent passing through said overflow vessel. As a result of this arrangement, a solution with a defined sample content may be taken from said flow, either continuously or discontinuously at any given time, and subjected to analysis. The samples, particularly those with a proportion of fine grains tending to adhere to the conveyor, may be removed quantitatively from the conveyor of the metering conveyor scale by means of a wiper blade and transferred to the overflow vessel. The metering conveyor scale is thus capable of processing samples with different grain ranges without difficulty. Because the falling distance of the material to be metered in only a few millimeters in the case of the metering conveyor scale in contrast to the tilting scale, there is practically no generation of dust. If the solvent is water and the public water supply system is at an adequately constant pressure, the constant flow of the solvent in the overflow vessel may be effected in the simplest case by means of a connection to the public water line and the insertion of a throttle valve. If these conditions cannot be satisfied, it will be sufficient to use a supply tank placed at a sufficient height above the overflow vessel in which tank the level of solvent is kept constant by suitable measures, such as a constant inflow and overflow, and which is connected to the overflow vessel by means of a line comprising a throttle valve.

Conveniently, a supply controlled metering conveyor scale is employed as the metering conveyor scale. Such metering conveyor scales with a vibratory feeder as the supplying device are commercially available, together with their controls. Advantageously, the vibratory feeder is preceded by a funnel with an overflow. The funnel serves as an intermediate storage facility for the sample which is supplied discontinuously by the sampler. The vibratory feeder draws the sample from the funnel and supplies it to the metering conveyor. The volume of the funnel, as determined by the overflow, is conveniently slightly larger than the amount of the sample drawn off by the vibratory feeder during the period of time between deliveries of the sample, so that there will be no discontinuity in the flow of sample transported by the metering conveyor scale.

In order to ensure that the soluble components of the samples are completely dissolved in the overflow vessel and mixed with the solvent, the overflow vessel is divided into at least two chambers. The metering conveyor scale feeds the sample to the upstream chamber, and the sample solution is withdrawn from the downstream chamber, preferably close to the overflow, for example by means of automatic pipettes, metering pumps or the like. Conveniently, the dissolution and mixing of the sample in the chambers is promoted by means of suitable devices, such as agitators or deflecting or overflow baffles.

Should the sample contain insoluble components, it is possible by suitable design of the flow cross sections within the chambers in combination with a suitable flow, to ensure that the insoluble components will be entrained in the flow. The insoluble components may be filtered out from the withdrawn sample solution prior to the analysis by continuous filters of the type known in the art.

If, for example, dilute aqueous acids are used in place of water as the solvent, the overflow vessel is advantageously provided with a third chamber whereby concentrated acid is introduced into the first chamber located along the direction of the flow; the sample is metered into the second chamber, and the sample solution is taken, as usual, from the last chamber.

Figure 1:
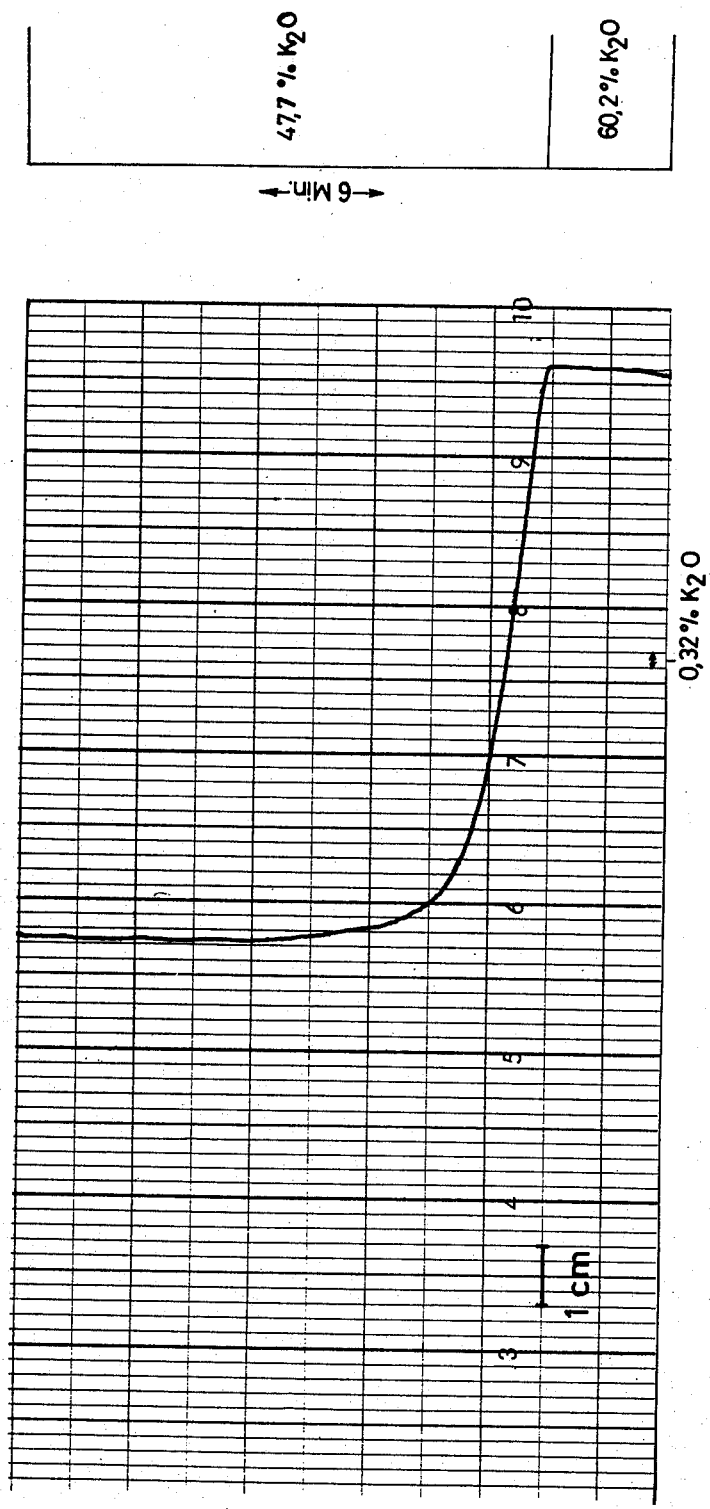
FIGS. 1 and 3 are graphs of test results showing the effectiveness of the invention.

The utility of the device according to the present invention was tested by determining the $K_2O$ content of potassium fertilizer salts having a known $K_2O$ content by means of thermometric indication in a continuous flow-through process. The recorder chart of FIG. 1 shows the successive analysis of two potassium fertilizer salts having different $K_2O$ contents, i.e., 47.7% $K_2O$ and 60.2% $K_2O$. Each division of the scale of the diagram corresponds to a $K_2O$ content of 0.32%. The paper feed was set at 20 centimeters per hour.

The accuracy of the analysis results at a $K_2O$ content of approximately 60% and a confidence limit of 95% was generally better than ±0.2% $K_2O$ absolute. In the thermometric analysis depicted in the recorder chart of FIG. 1, the error amounted to ±0.1% $K_2O$ absolute. Preliminary experiments using other samples and other methods of analysis indicate that results with deviations of similar orders of magnitude can be expected.

DETAILED DESCRIPTION OF A PREFERRED EMBODIMENT

Figure 2:
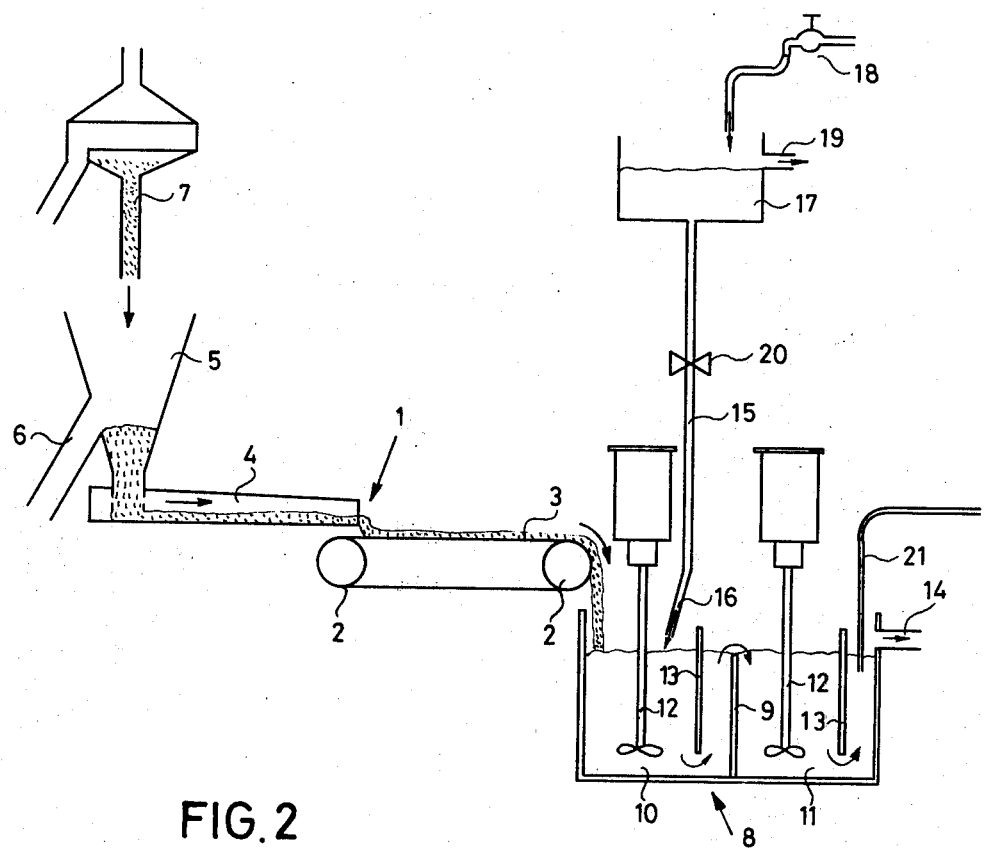
FIG. 2 is a schematic representation of a preferred apparatus according to the invention.

An example of a preferred embodiment of the present invention is represented schematically in a front elevation in FIG. 2.

The drawing shows a metering conveyor scale designated generally by reference numeral 1, which essentially comprises a conveyor 3 running around end rollers 2, a vibratory feeder 4 and drive, weighing and control devices (not shown). Metering conveyor scales of this type with controlled feed rates are commercially available (for example, metering conveyor scale model EDB from Hans Boekels GmbH. & Co. of Aachen, Federal Republic of Germany). The speed of the conveyor 3 is adjustable but is maintained constant in operation. Control of the sample supply is effected by adjusting the vibration amplitude of the vibratory feeder 4.

A funnel 5 with overflow 6 is disposed above the receiving end of the vibratory feeder. It serves as an intermediate storage facility for the sample which is supplied discontinuously by a conventional sampler 7.

A dissolving or overflow vessel, generally designated by reference numeral 8, is disposed underneath the discharge end of conveyor 3. The overflow vessel is divided by means of an overflow baffle 9 into two chambers 10 and 11. Each chamber 10 and 11 is equipped with an agitator 12 and a deflecting baffle 13 downstream of said agitator in the direction of the flow. The deflecting baffles 13 are immersed nearly to the bottom of the overflow vessel and extend above the surface of the solvent, the depth of which is determined by the discharge overflow 14. Overflow baffle 9 conveniently is of the same height as the overflow 14. By suitable design of the flow paths in combination with a suitable flow velocity, entrainment of possibly present insoluble components of the sample by the solvent flow may be achieved.

Overflow vessel 8 is connected to a solvent tank 17 by means of a line 15 opening at 16 into the upstream chamber 10. The constant supply of the solvent at 18 (e.g., from a public water supply system) and the use of an overflow 19 ensure a constant level of the solvent in the tank 17. The flow of the solvent to the overflow vessel 8 may be regulated by means of a control valve 20 interposed in line 15.

The solvent, the sample and the sample solution pass along the path designated by the arrows. Near the overflow 14 of the vessel 8, a desired portion of the sample solution may be taken up at 21, for example with automatic pipettes, metering pumps or the like. If the sample contains insoluble components, the sample solution taken at 21 may be passed prior to analysis through a known type of continuous filter (not shown).

The device operates in the following manner: following the opening of the solvent inlet 18, the overflow vessel 8 is filled with solvent and the flow of the solvent adjusted at 20 to a predetermined value. After this, or more or less simultaneously with it, the agitators 12 are activated. Metering conveyor scale 1 is also activated and its conveying rate adjusted to a predetermined level. Once the device has been readied in this manner, the first sample may be supplied by the samples 7. In a continuous control operation, for example to control production processes, the amount of sample supplied is preferably somewhat larger than the transport capacity of the metering conveyor scale, so that no discontinuity will occur in the sample solution.

After a brief buildup period following initiation of the metering of the sample into the overflow vessel, a portion of the sample solution may be withdrawn for analysis at 21.

Figure 3:
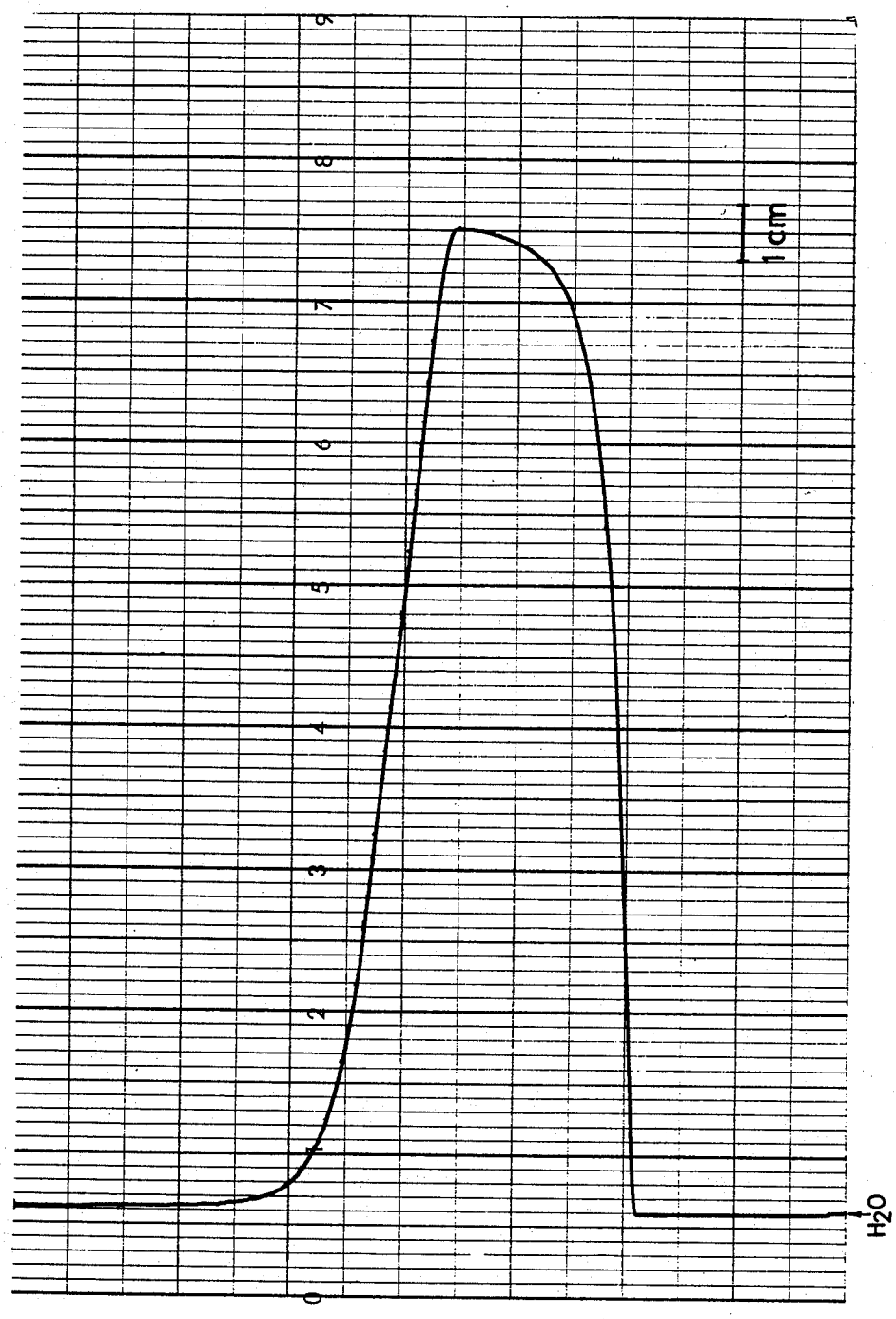

When only occasional analyses are required, it is sufficient to supply individual samples at suitable time intervals. In the case of continuous flowthrough analyses, a recorder chart such as that illustrated in FIG. 3 is obtained.

In the above-mentioned determination of the $K_2O$ content of potassium fertilizer salts, intended for use with a process of purifying said salts by flotation, the sampler furnished approximately 600 g salt every 5 minutes. The holding capacity of the funnel 5 determined by the funnel overflow 6 was set at approximately 550 g. The transport capacity of the metering conveyor scale was adjusted to 100 g of salt per minute so that a minimum of 50 g salt remained in the funnel as a reserve. Thus, approximately 100 g of each subsequent salt sample were discarded by means of the overflow 6. The solvent flow rate into the overflow vessel 8 was set at 500 ml per minute so that the sample solution had a concentration of 0.2 g sample per ml.

I claim:

1. Apparatus for preparing solutions of solids samples for wet chemical analysis, said apparatus comprising:
   (a) an overflow dissolving vessel, divided by an overflow baffle into at least two chambers,
   (b) means for maintaining a constant stream of solvent flowing successively through the chambers of said overflow dissolving vessel, and
   (c) metering conveyor scale means for continuously metering a measured amount of a solid sample to be analyzed to the overflow dissolving vessel.

2. Apparatus according to claim 1 wherein said metering conveyor scale is a feed controlled metering conveyor scale.

3. Apparatus according to claim 2 wherein said feed controlled metering conveyor scale comprises a vibratory feeder as the feed device and an overflow funnel for supplying sample to the vibratory feeder.

4. Apparatus according to claim 1 wherein each chamber in said overflow dissolving vessel is equipped with means for promoting dissolution and mixing of a sample in said solvent.

5. Apparatus according to claim 4 wherein said dissolution and mixing promoting means comprises an agitator in such chamber.

6. Apparatus according to claim 4 wherein said dissolution and mixing promoting means comprises a deflecting baffle in each chamber.

7. Apparatus according to claim 1 wherein said means for maintaining a constant stream of solvent flowing through said dissolving vessel comprises means for supplying solvent at substantially constant pressure to said vessel, throttle valve means on said solvent supply means and overflow means for maintaining a constant level of solvent in said vessel.

8. Apparatus according to claim 1 further comprising means for automatically withdrawing a sample of solution from said vessel for analysis.

9. Apparatus according to claim 8 wherein said overflow means and said solution withdrawing means are disposed at a remote location from the point where the solid sample to be analyzed is continuously metered into the dissolving vessel.

10. Apparatus according to claim 4 wherein solid sample to be analyzed is continuously metered into one of said chambers and overflow means and solution withdrawing means are disposed in the other of said chambers.

* * * * *